United States Patent
Kangasniemi et al.

(10) Patent No.: US 6,881,062 B2
(45) Date of Patent: Apr. 19, 2005

(54) METHOD AND PRODUCT FOR SHAPING A FIBRE PRODUCT FOR DENTAL USE

(75) Inventors: Ilkka Kangasniemi, Turku (FI); Pekka Vallittu, Kuusisto (FI)

(73) Assignee: Stick Tech Oy, Turku (FI)

( * ) Notice: Subject to any disclaimer, the term of this patent is extended or adjusted under 35 U.S.C. 154(b) by 290 days.

(21) Appl. No.: 10/169,457

(22) PCT Filed: Jan. 11, 2001

(86) PCT No.: PCT/FI01/00020

§ 371 (c)(1),
(2), (4) Date: Jul. 1, 2002

(87) PCT Pub. No.: WO01/50979

PCT Pub. Date: Jul. 19, 2001

(65) Prior Publication Data

US 2003/0003423 A1 Jan. 2, 2003

(30) Foreign Application Priority Data

Jan. 12, 2000 (FI) .............................. 20000053

(51) Int. Cl.[7] .................................. A61C 5/04
(52) U.S. Cl. ...................... 433/226; 433/141; 433/219; 433/229
(58) Field of Search ................................ 433/215, 216, 433/219, 141, 229, 226

(56) References Cited

U.S. PATENT DOCUMENTS

| | | | |
|---|---|---|---|
| 2,641,836 A | 6/1953 | Morrison | |
| 2,937,446 A | * 5/1960 | Weisenfeld | 433/146 |
| 3,628,249 A | 12/1971 | Wurl | |
| 4,073,530 A | 2/1978 | Seidler | |
| 4,522,594 A | 6/1985 | Stark et al. | 433/141 |
| 4,975,053 A | * 12/1990 | Hofsess | 433/25 |
| 4,993,949 A | * 2/1991 | Hill | 433/141 |
| 5,014,532 A | * 5/1991 | Shoher et al. | 72/60 |
| 5,176,951 A | 1/1993 | Rudo | 428/229 |
| 5,256,064 A | * 10/1993 | Riihimaki et al. | 433/141 |
| 5,358,404 A | 10/1994 | Schumacher | 433/164 |
| 5,527,181 A | * 6/1996 | Rawls et al. | 433/149 |
| 5,829,979 A | 11/1998 | Kobashigawa et al. | 433/180 |
| 6,039,566 A | * 3/2000 | Foser | 433/60 |

FOREIGN PATENT DOCUMENTS

| | | |
|---|---|---|
| DE | 42 19 793 | 10/1993 |
| EP | 668 060 | 8/1995 |

* cited by examiner

Primary Examiner—Cary E. O'Connor
(74) Attorney, Agent, or Firm—James C. Lydon

(57) ABSTRACT

The invention relates to a method and silicone product for shaping a fibre product used in dentistry to reinforce a prosthetic appliance or a similar structure under construction to conform to the final location. The fibre product containing fibres and curable material is pressed by means of silicone material against the final location or a model thereof followed by curing the curable material present in the fibre product. The invention is characterized in that the silicone material is a polymerised, elastic and soft silicone material that has been shaped to a piece (10,11) corresponding to the size and shape of the fibre product to be shaped, and that when pressed, the silicone material adopts the shape of the final location or the model thereof.

12 Claims, 2 Drawing Sheets

METHOD AND PRODUCT FOR SHAPING A FIBRE PRODUCT FOR DENTAL USE

Figure 1:
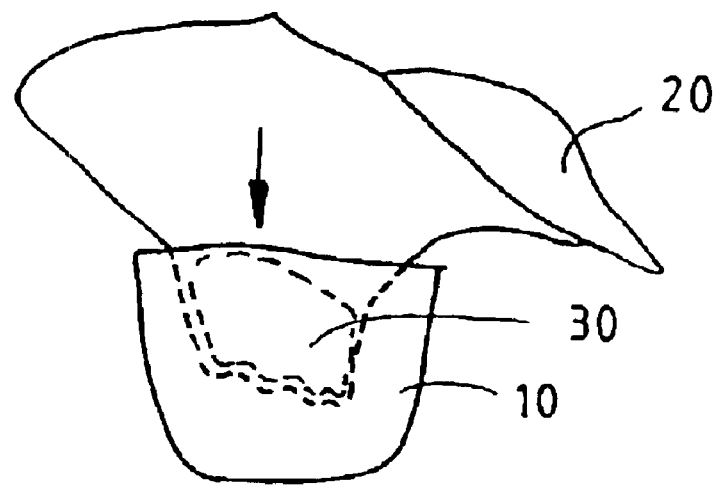

This application is a U.S. National Stage of International application PCT/FI01/00020, filed Jan. 11, 2001, and published on Jul. 19, 2001 in the English Language.

The invention is directed to a method and product for shaping a fibre product used in dentistry, as defined in independent claims.

Fibre products such as fibre fabrics and fibre bundles are commonly used in dentistry for splinting teeth and for reinforcing and repairing various dental prosthetic appliances such as crowns, fixed bridges, removable dentures and so-called surface attachable bridges (i.e. light or maryland bridges), and facades. Such fibre reinforcing products may either solely consist of fibres, or be fibre reinforcing products preimpregnated with a polymer or a monomer. Fibre products having the desired shape are obtained by curing the polymers and/or monomers present in the products for instance with blue light. Fibre products (both preimpregnated and non-impregnated) are commercially available. Fibre products remain in the final products as reinforcements and accordingly, they should be shaped precisely to conform to the final location (e.g. a supporting tooth) before curing and constructing a desired structure thereon (a bridge, removable denture or like).

For several reasons, silicone moulds are commonly used in dentistry to obtain a precise impression of the denture, or prepared supporting teeth in the mouth. Silicones are used to construct exact plaster models. If it is desirable to shape a fibre product (fibre fabric or bundle), said fibre product must be pressed on the model or tooth and cured to make the fibres fit to the surface of the denture to be constructed as snugly as possible.

The problem is that the forming of the mould is time-consuming and considerably increases the cost of the final product.

Particularly, the construction of a complete crown bridge is complicated. Crown bases for each supporting tooth must be made from the fibre fabric in separate steps. Then these crown bases must be joined to each other with a fibre bundle having unidirectional fibres. To shape the fibre product, it is necessary to make a mould of the area, against which the fibre product will be placed. It is important to press the products to an intimate contact with the surface since the working space is very restricted and it is preferable for the strength of the final structure to contain as much fibres as possible.

Since each crown base needs its own mould and it takes about 5 minutes to make one mould, it is rather time-consuming to make the moulds for all crown bases of the bridge. It is very difficult to carry out this procedure in the mouth of a patient. At present, the moulds for crown bases are made from a thermally softened plastic plate. A model (removable supporting tooth made of plaster) is pressed against this softened plastic plate. After cooling, the plastic plate adopts the shape of the supporting tooth. Thereafter, excess material is cut away and the trimmed mould thus obtained may be pressed against the supporting tooth so that the fibre fabric is placed between the mould and the supporting tooth. After pressing the mould against the supporting tooth, the fibre fabric is cured with light. The fibrous crown base now has the shape of the supporting tooth.

Another way to make the mould is to inject transparent silicone to the final location of the aimed structure in the mouth, or to the model of this final location, thus obtaining a copy of all the sites lying under the silicone. The silicone mass is polymerised. This way is faster since moulds for several supporting teeth are obtained in one step. However, this method is expensive since high amounts of the valuable silicone material are consumed. Moreover, additional steps are needed to place a fibre product (for instance a fibre web) between the mould and the supporting teeth. Therefore, part of the mould material must be removed, if necessary. Alternatively, the mould may be waxed before pressing the silicone mass against it.

The object of the present invention is to eliminate the need to make the mould and provide a method for shaping the fibre product to conform to the final location (the supporting teeth in the mouth or the model thereof) of the aimed structure without a separate mould.

Another object of the invention is to provide means that is suitable for this shaping and may be reused.

The above objects of the present invention are attained with the method and means of the invention, which are characterized by what is disclosed in the characterizing part of the apended claims.

Accordingly, the present invention relates to a method for shaping a fibre product used in dentistry to reinforce a prosthetic appliance or a similar structure under construction to conform to the final location, wherein the fibre product containing fibres and curable material is pressed by means of silicone material against said final location or a model thereof followed by curing the curable material present in the fibre product. The invention is characterized in that said silicone material is a polymerized, elastic and soft silicone material that has been shaped to a piece corresponding to the size and shape of the fibre product to be shaped, and that when pressed, the silicone material adopts the shape of the final location or the model thereof.

The invention also relates to a silicone product that may be used to shape a fibre product containing fibres and a curable material used in dentistry to reinforce a prosthetic appliance or a similar structure under construction to conform to the final location by pressing said fibre product by means of silicone material against said final location or a model thereof, followed by curing the curable material present in the fibre product. The silicone product according to the invention is characterized in that said silicone material is a polymerised, elastic and soft silicone material that has been shaped to a piece corresponding to the size and shape of the fibre product to be shaped, and that when pressed, said silicone material adopts the shape of the final location or the model thereof.

Depending on the application, the fibre product may for instance be a fibre bundle or a bunch with unidirectional fibres, or a mat having fibres oriented in various directions. A fibre bundle may be used to reinforce splints, for instance, whereas mats suit for the reinforcement of crown bases. The fibre product may solely consist of fibres, e.g. glass fibres, or it may for instance be preimpregnated with a curable material (polymer or monomer). Should the fibre product not contain all the necessary constituents needed for curing, it is of course important to add them to the fibre product before the use thereof.

The expression "silicone material has been shaped to a body corresponding to the size and shape of the fibre product to be shaped" means that the size and shape of the body are sufficient and suitable for the shaping of the fibre product.

The term "final location" means the site where the final fibre reinforced structure under construction is to be attached. Thus, the site may be the teeth in the mouth of the patient (supporting teeth) that are most often abraded, or prepared in another way, or unprepared crowns or a part of a removable prosthetic appliance.

The fibre product may be shaped for the actual final location. Alternatively, an exact model (for instance, a plaster model) of the final location may be made first followed by shaping the fibre product against this model.

Particularly, the term fibre reinforced "structure" means constructions for splinting teeth and various dental prosthetic appliances such as crowns, fixed bridges, removable dentures and so-called surface attachable bridges (i.e. light or maryland bridges).

The silicone product of the invention consists of polymerised silicone material known as such. The elasticity and softness of the polymerised silicone material are important to its ability to exactly conform to the final location or the model thereof. The hardness (shore hardness) of the silicone material, characterizing the elasticity thereof, is between A2 and A25, preferably below A15, most suitably about A8. The hardness below A15 allows the material to conform to the shape of substantially three-dimensional bodies such as teeth.

Very soft (gel-like) silicone materials must be enclosed in a film or a similar layer for cohesion reasons.

Curing of the fibre product is normally accomplished with light (for instance, blue light). Alternatively, the curing will be carried out as auto-polymerization. When curing with light the silicone material must transmit the curing light, most preferably be transparent.

The invention is now described in more detail by referring to the appended drawings.

FIG. 1 shows a piece 10 according to the invention made of polymerized silicone, having approximately a cubical shape. The shape and size of the piece are suitable to shape a fibre fabric 20 to conform to a crown base 30. The crown base 30 is pressed on the elastic and soft silicone piece 10 so as to leave the fibre fabric 20 between the crown base and silicone material. In this position, the fibre fabric (containing all the constituents necessary for curing) is cured for instance with light. Curing, that is shaping of the fibre fabric, takes only few seconds.

Figure 2:
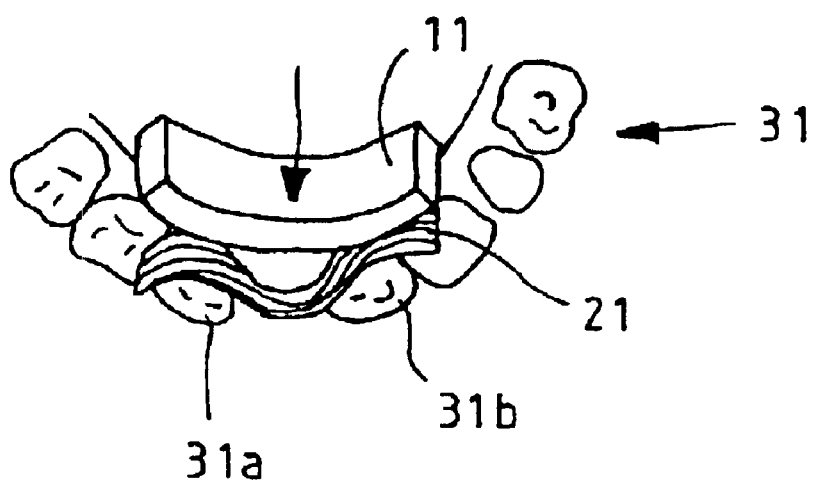
Figure 3:
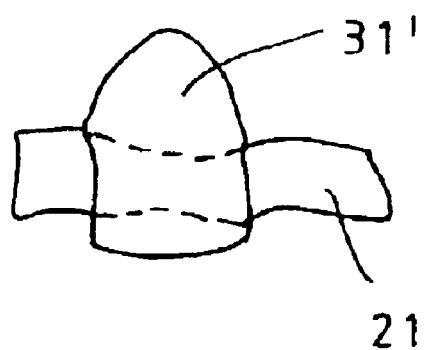

FIG. 2 shows a row of teeth 31 in the mouth of a patient lacking one tooth that will be replaced by an artificial tooth 31' (see FIG. 3). A fibre bunch 21 is laid on the lacking tooth and adjacent teeth 31a and 31b and the fibre bundle is pressed against the final location by means of an elongated silicone piece 11. It is preferable that the surface area of the piece 11 being pressed against the fibre product is approximately a flat surface (an even surface or a level).

FIG. 3 shows an artificial tooth 31' having the shaped fibre bundle 21 as a reinforcement. This reinforced artificial tooth is implanted to the row of teeth of the patient with a method known as such.

Figure 4:
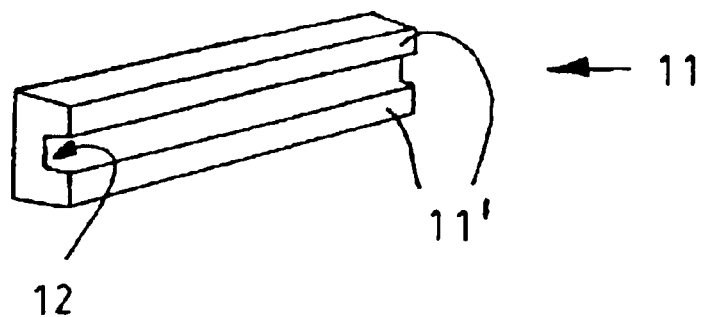

FIG. 4 shows an elongated silicone piece 11 according to another embodiment. On the flat surface 11' of the piece 11, there is a longitudinal slot 12 for the fibre bundle 21. Due to the slot the separate fibres of the moistened fibre bundle remain unidirectional. In one version, for instance a preimpregnated fibre bundle is already adjusted into the slot of the silicone piece 11. In another version, the user himself inserts the fibre bundle into the slot of the silicone piece.

Figure 5:
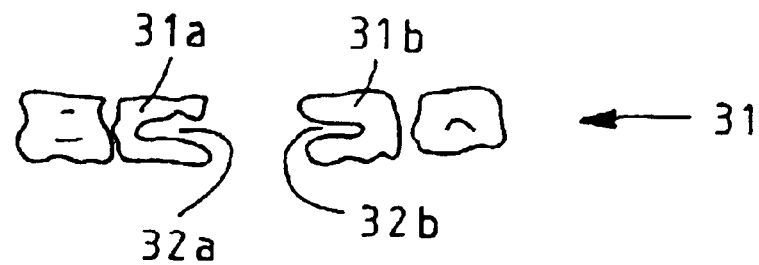

FIG. 5 shows a row of teeth 31 of a patient, wherein two teeth 31a 31b with one tooth lacking between them are having slots 32a and 32b for the bridge to be constructed. To make the fibres of the fibre product to be pressed tightly against the surfaces of the slots 32a and 32b, it is preferable that the elongated silicone piece 11 has the shape of a cylinder longitudinally cut through, preferably a semicylindrical piece (see FIG. 6). The curved surface on the piece 11 is used to press the fibre product against the surfaces of the slots 32a and 32b made on the teeth.

It is also possible to combine different shapes of the silicone pieces.

Figure 6:
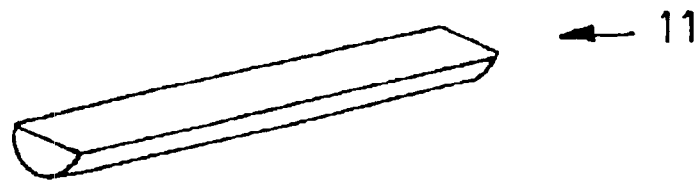
Figure 7:
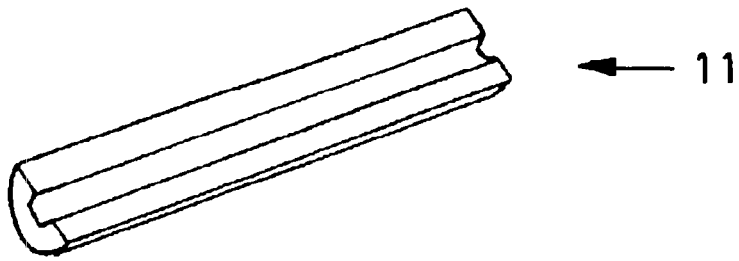

FIG. 7 shows a silicone piece with a semicylindrical form as in FIG. 6 and having a slot 12 made on the flat surface 11' thereof (see FIG. 4). According to another embodiment (not shown in Figures), this slot 12 for instance conforms to the masticatory surfaces of the teeth or simulates them and is deeper in the middle of the piece than in the edge areas thereof. According to yet another embodiment, there is a depression simulating the shape of an individual tooth on the flat surface of the piece (not shown in the Figures).

After pressing, the initial shape of the elastic silicone pieces will recover and, thus, they may be reused to shape other similar fibre products.

The main advantage of the invention is the saving of time owing to the fact that the preparation of the mould, particularly different moulds, is avoided, and the saving of the silicone material since it may be reused.

The embodiments of the invention described above are only examples of the practical application of the inventive idea. It is clear to those skilled in the art that various embodiments of the invention may vary within the scope of the appended claims.

What is claimed is:

1. A method for shaping a fibre product used in dentistry to reinforce a prosthetic appliance or a similar structure under construction to conform to a final location, comprising pressing a fibre product containing fibres and curable material against said final location or a model thereof by means of a silicone material, subsequently curing the curable material present in the fibre product, wherein said silicone material is a polymerized, elastic and soft silicone material that has been shaped to a body corresponding to the size and shape of the fibre product to be shaped, and wherein, when pressed, the silicone material adopts the shape of said final location or a model thereof.

2. The method of claim 1, wherein the silicone material is a silicone transparent to curing light and having a hardness (shore hardness) between A2 and A15.

3. The method of claim 2, wherein said silicone material has a hardness of A8.

4. A silicone product that may be used to shape a fibre product containing fibres and curable material used in dentistry to reinforce a prosthetic appliance or a similar structure under construction to conform to a final location by pressing said fibre product by means of silicone material against said final location or a model thereof, followed by curing the curable material present in the fibre product, wherein said silicone material is a polymerized, elastic and soft silicone material that has been shaped to a body corresponding to the size and shape of the fibre product to be shaped, and when pressed, the silicone material adopts the shape of the final location or the model thereof, wherein the silicone material is silicone transparent to light used to cure said curable material, and wherein said silicone material has a hardness (shore hardness) between A2 and A15.

5. The silicone product of claim 4, wherein the silicone material has a hardness of 8.

6. The silicone product of claim 4, wherein a size of said silicone material is such that it allows a supporting tooth covered with a fibre fabric to be pressed into said silicone material.

7. The silicone product of claim 6, wherein said silicone material has approximately a cubical shape and at least one substantially flat surface.

8. The silicone product of claim 4, wherein said silicone material is an elongated piece having the shape of a cylinder longitudinally cut through, the curved surface of which is adapted to press the fibre product into the slots made on teeth to construct a bridge base.

9. The silicone product of claim 8, wherein said elongated piece is semicylindrical.

10. The silicone product of claim 4, wherein the product is an elongated piece having at least one longitudinal, substantially flat surface.

11. The silicone product of claim 10, wherein said flat surface has a longitudinal slot, said slot being optionally deeper in a middle of the piece than in an edge area thereof.

12. The silicone product of claim 11, wherein said flat surface has a depression simulating the shape of an individual tooth.

\* \* \* \* \*